United States Patent [19]

Plicchi et al.

[11] Patent Number: 4,596,251
[45] Date of Patent: Jun. 24, 1986

[54] MINUTE VENTILATION DEPENDENT RATE RESPONSIVE PACER

[76] Inventors: Gianni Plicchi, Via Mascarella 77/7; Giancarlo Canducci, Via Cesare Pavese 27, both of Bologna, Italy

[21] Appl. No.: 659,542

[22] Filed: Oct. 10, 1984

[30] Foreign Application Priority Data

Feb. 7, 1984 [IT] Italy ............................ 12421 A/84
Jun. 5, 1984 [IT] Italy ............................ 12535 A/84

[51] Int. Cl.⁴ ............................................. A61N 1/36
[52] U.S. Cl. ........................ 128/419 PG; 128/723; 128/725
[58] Field of Search ......... 128/419 PG, 716, 721–725, 128/734

[56] References Cited

U.S. PATENT DOCUMENTS

| | | | |
|---|---|---|---|
| 3,593,718 | 7/1971 | Krasner | 128/419 PG |
| 3,802,419 | 4/1974 | Yates | 128/723 |
| 3,874,368 | 4/1975 | Asrican | 128/734 |
| 4,074,710 | 2/1978 | Tiep | 128/716 |

FOREIGN PATENT DOCUMENTS 2026870  2/1980  United Kingdom ......... 128/419 PG

*Primary Examiner*—William E. Kamm
*Attorney, Agent, or Firm*—Spencer & Frank

[57] ABSTRACT

An electronic circuit included in a pacer detects the impedance between two electrodes connected to it and made up by the conducting part of the pacer case (B) and by an auxiliary subcutaneous lead placed in the chest or by an electrode placed on the insulating part (C) of the case itself. The changing geometry of the chest, due to pulmonary ventilation, determines the impedance variations. The electronic circuit, by processing the impedance signal is able to automatically adjust the stimulation rate of the ventricle and/or of the atrium between minimum and maximum preset values according to the activity levels of the patient.

17 Claims, 13 Drawing Figures

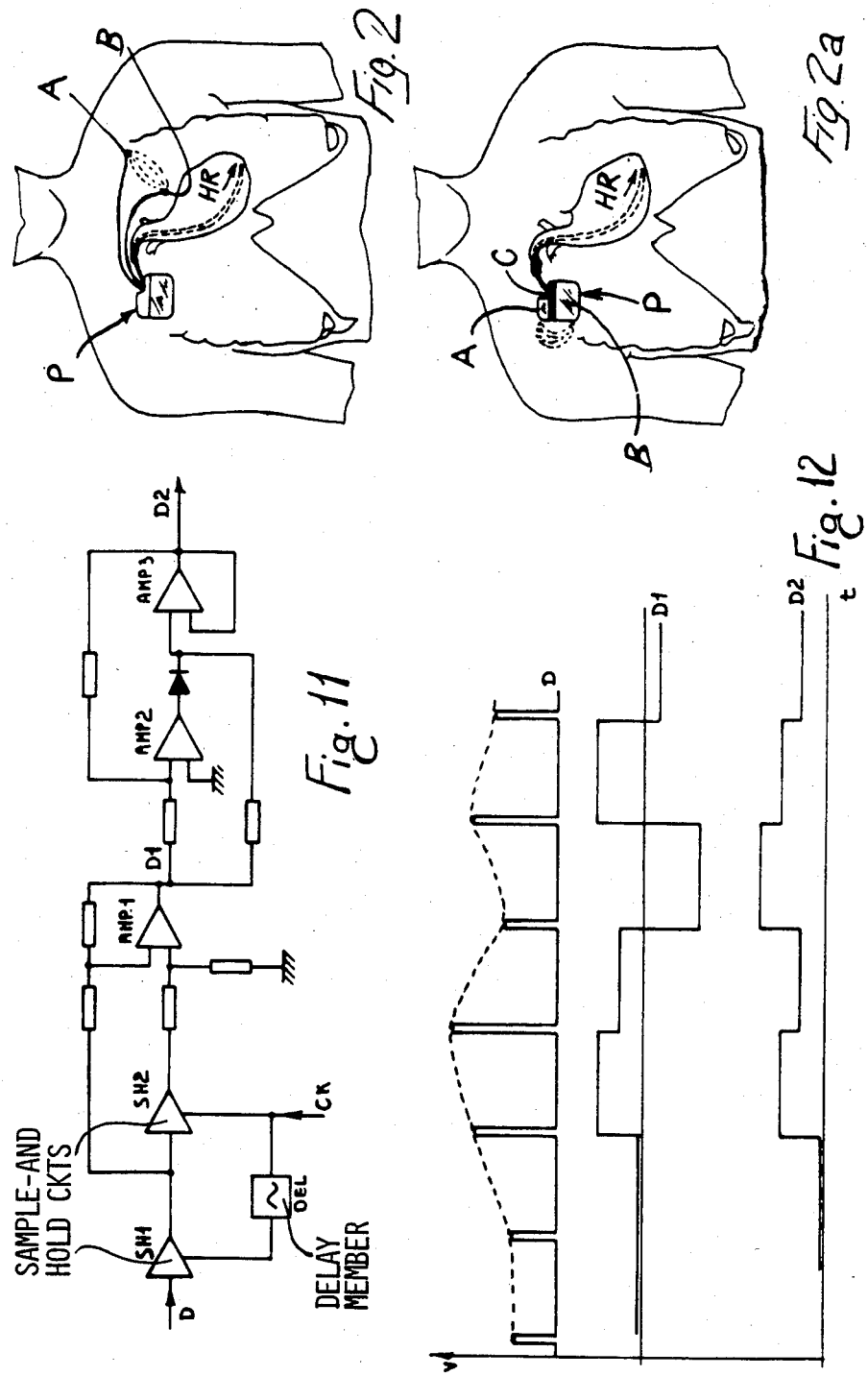

MINUTE VENTILATION DEPENDENT RATE RESPONSIVE PACER

BACKGROUND AND SUMMARY OF THE INVENTION

The invention relates to implantable cardiac pacers and more particularly to a rate responsive pacer which automatically alters the stimulation rate of the heart in response to the metabolic demand of the patient. At the present stage, a wide range of cardiac pacers is used to replace, by an implantable device, the mechanisms producing and driving the electrical signals associated with the heart function in the human body. These pacers are identified by internationally agreed abbreviations. Hereafter we will use the word "Pacemaker" (registered trademark) in place of implantable cardiac electrostimulator. The pacers wherein the stimulation of the ventricle is driven and synchronized with the naturally occurring activity of the atrium are generally considered physiologic as the artificial stimulation rate is not preset but is induced by the atrial natural activity and is, therefore, always proportional to the latter one. As a consequence this kind of pacemaker can be used only in those cases wherein the atrial activity is physiologic, that is, only 30/60% of the present pacemaker patients. Hence, in the present conditions a high percentage of patients cannot use an electrostimulation based on a physiologically variable rate according to the above description. This is the reason why many experts have long tried to realize an implantable pacemaker able to detect an alternative parameter other than the atrial activity, parameter which can change in response to the physiologic demand of the patient and can be used as a reference variable in order to automatically and physiologically regulate the heart electrostimulation rate. As yet the pacemakers theorized and designed to solve said problem are those hereafter summarized wherein the electrostimulation rate is subject by an algorithm to changes in the following parameters: atrial activity—blood pH—body temperature—oxygen saturation in venous blood—QT interval obtained from the endocavitary E.C.G.—respiratory rate—mechanical activity—cardiac output—electromyogram of the diaphragm. An overall discussion on the characteristics of these proposals can be found in:

Clin. Prog. Pacing and Electrophysiol. Vol. 1 n. 1—1983 "Rate Responsive Pacing" by Anthony F. Rickards M.D. and Robert M. Donaldson M.D.—From the National Heart Hospital—London W 1 England - and in:

"A Physiologically Controlled Cardiac Pacemaker'-'—Krasner—Voukydis and Nardella—J.A.A.M.I., Vol. 1 n. 3—1966; 14-20—
and more specifically in:

"A Pacemaker which automatically increases its rate with physical activity" by Kenneth Anderson, Dennis Brumwell, Steve Huntley—From Medtronic Inc.—Minneapolis—Minn.—U.S.A.
and:

"Variation of Cardiac Pacemaker rate relative to respiration"—IEEE/Engineering in Medicine and Biology Society First Annual Conference—p. 50, 1979—by Getzel W., Orlowski J., Berner B., Cunnigham B., Esser M., Jacob M., Jenter D. Other pacemakers of the kind are described in the European patent application No. EP-A-0 080 348 as well as in U.S. Pat. Nos. 3,593,718—4,228,803—4,313,442—4,202,339—4,140,132—4,009,721—and in the European patent application No. EP-A-0 089 014 and corresponding U.S. application Ser. No. 06/474,241 filed by the same applicants of the present application.

All the literature highlights the existing need and desire to realize a pacemaker able to adjust the stimulation rate to the metabolic demand by means of a suitable physiologic variable sensor circuit. The present invention consists of a rate responsive pacer the inhibition and/or stimulation rate of the ventricle and/or of the atrium of which is automatically driven in the range between minimum and maximum programmable values by a measuring and processing circuit which detects the variations in time of the geometry of a part of the chest of the patient as a consequence of pulmonary ventilation. The circuit also produces a signal which depends on said physiologic variable and which automatically changes the pacemaker stimulation rate between said minimum and maximum values.

DESCRIPTION OF THE DRAWINGS

The features of such a pacemaker and its resulting advantages are apparent in the following description of a preferred embodiment, shown by way of non-limiting example, in the annexed sheets of drawings, in which:

FIG. 2, 2a and 3 show different possible arrangements of the pacer and of its electrodes and leads in the patient's body;

FIG. 11 shows an example of wiring diagram of the second block of the circuit of FIG. 5;

FIG. 12 shows signals processed by the circuit of FIG. 11.

DESCRIPTION OF THE PREFERRED EMBODIMENT

Figure 1:
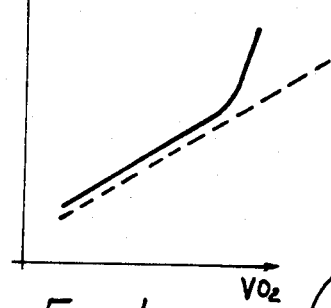
FIG. 1 is a diagram showing the normal relation in man between pulmonary minute ventilation and oxygen consumption.

Pulmonary minute ventilation (VE), as shown in FIG. 1 of the annexed drawings, strictly depends on $VO_2$ oxygen consumption in man and is controlled by chemical-humoral and nervous stimuli, similarly to the heart activity. It is important to note that the ventilation which is defined as liters of air inhaled during the time unit is quite different from the respiratory rate which is defined as the number of respirations in the time unit. While the respiratory rate measurement is simply confined to the detection of the presence or absence of the breathing act, apart from its duration and amplitude, the minute ventilation requires continuous direct or indirect measurement of the airflow in and out of the lungs. Moreover, the respiratory rate, as we will see in the following examples, is not always an indicator of physical activity, whereas the proportional correlation between minute ventilation and oxygen consumption up to the anaerobiosis threshold is well proven and is accepted in all scientific literature. In fact, in absence of physical activity, for example in sleep, the respiratory rate may increase even if minute ventilation and oxygen uptake is reduced due to the minimal metabolic demand of the human body. On the other hand, the athletes, in order to increase the minute ventilation in response to the increased oxygen demand, are trained to increase the tidal volume more than the respiratory rate. As the minute ventilation increase occurs simultaneously to the exercise, similarly to cardiac activity, we suggest using minute ventilation as a reference parameter to control the heart artificial stimulation rate. In pulmonary ventilation, the variation in the inhaled and exhaled gas volume, in the preset time unit, corresponds to an equivalent variation in the chest cavity volume and, therefore, to its geometric variation.

Figure 5:
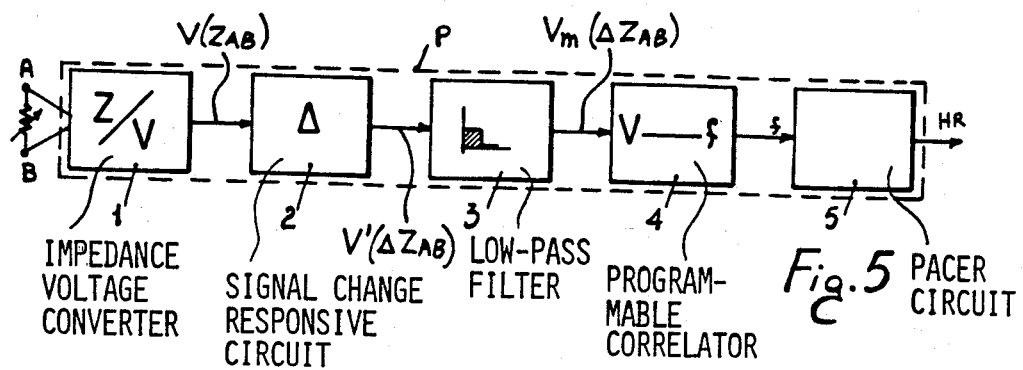
FIG. 5 shows the block diagram of a single chamber demand pacemaker which incorporates the invention.
Figure 3:
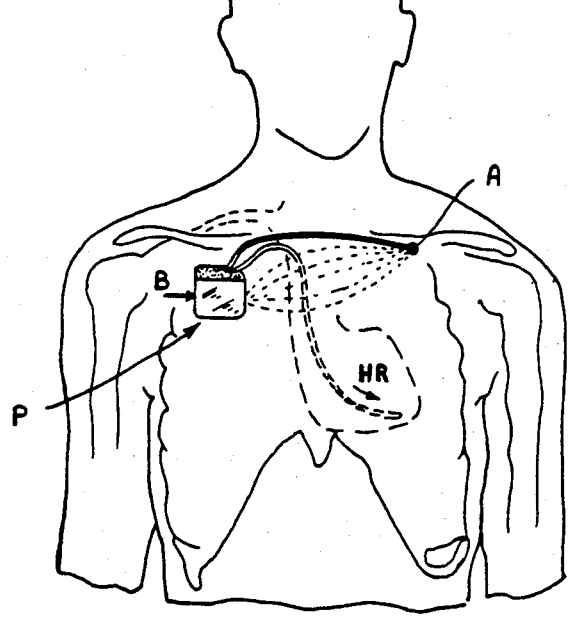
Figure 6:
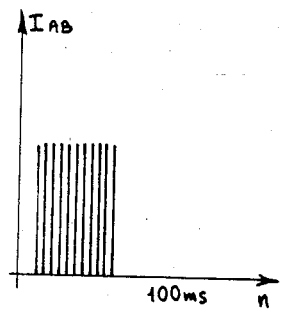
FIGS. 6, 7, 8, 9 and 10 show the input signals of the different blocks of the diagram of FIG. 5.
Figure 10:
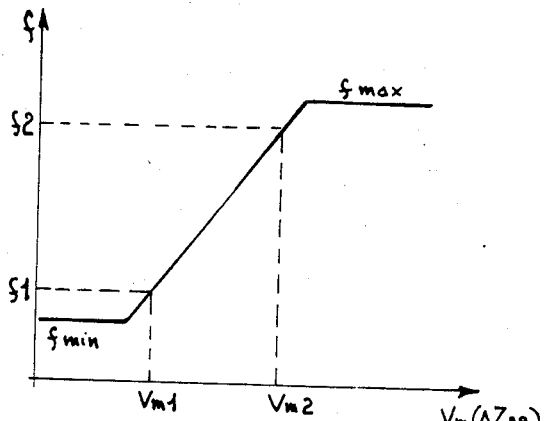

In order to detect the minute ventilation it is sufficient to detect the electrical impedance time variation of a part of the chest by means of two electrodes A and B subcutaneously positioned, for example with the arrangement show in FIG. 2 wherein an electrode could correspond to the heart stimulation lead or with the arrangement of FIG. 3 wherein an electrode (B) corresponds to the pacemaker conductive case (P) or with the arrangement of FIG. 2a wherein both electrodes A and B are placed on the pacemaker case and are separated by an electrically insulating part (C) of the same case. It is understood that electrode A can be placed in any suitable and non critical position vis-a-vis electrode B keeping in mind that such position has to allow the detection of geometric variations of a part of the chest barely affected by the movements of the upper limbs of the patient. In view of these premises we will now describe the block diagram of a single chamber demand pacemaker. FIG. 5 shows block 1 consisting of a strobed Impedance/Voltage converter using sampling frequencies of approx. 10 Hz and including means which allow to send very narrow pulses of proper intensity to the electrodes A and B. The duration and repetition period ratio of these pulses is very high, for example 1/1000. In this manner, the means designed for said impedance measurement consume a minimum quantity of energy and can therefore be supplied by the same electric battery supplying the implanted pacemaker without being remarkably detrimental to the life-time of the battery. A possible circuit with these features has been described in detail in No. EP-A-0 089 014 of the same applicants, as already mentioned. The strobed pulses between electrodes A and B are outlined in the diagram of FIG. 6.

Figure 7:
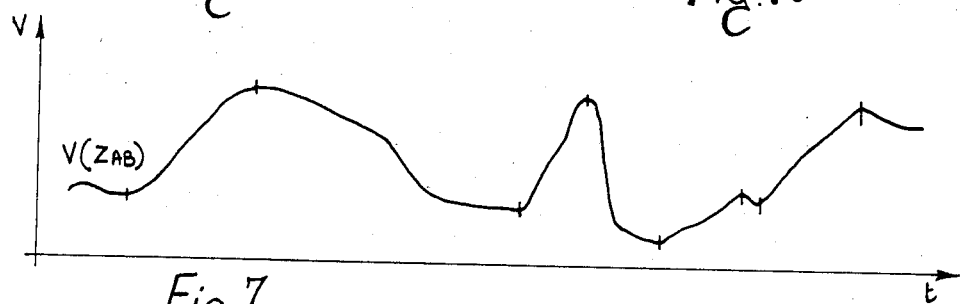
Figure 8:
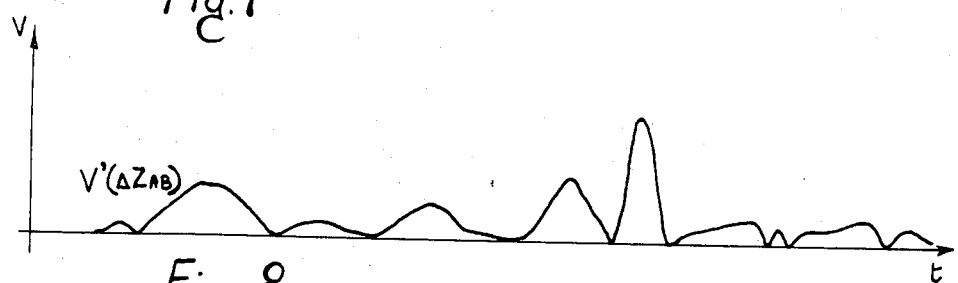

Block 2 consists of means to measure the absolute variations of the signal corresponding to the impedance between one pulse and the previous one. The function of block 2 is remarkable in that it allows to turn signal V ($Z_{AB}$) coming from block 1 (FIG. 7) into a signal V' ($\Delta Z_{AB}$) proportional to the chest volume variation speed, that is a signal proportional to the instantaneous respiratory flow, in absolute value, taking the flow itself as a variation in time of the chest volume. The signal, shown in FIG. 8, will have peaks corresponding to the phases of the respiratory cycle in which the expiratory and inspiratory speeds reach their maximum values and will have a zero value when any respiratory dynamics is absent.

Another peculiar function of block 2 consists in offsetting the slow variations of the impedance between electrodes A and B due for instance to the histologic changes in the tissues surrounding the same electrodes or due to the change in the relative position of the same electrodes or to the slow variation of the bodily mass of the patient or to the posture variation of the patient or, finally, to the variation of the lung residual functional capacity which shows a positive increase under strain conditions.

Figure 4:
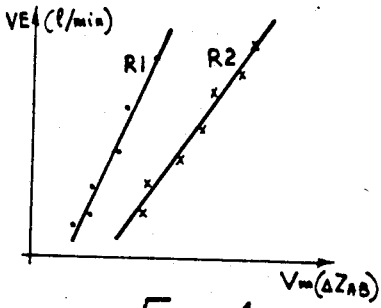
FIG. 4 shows two correlation slopes identifying minute ventilation (1/min) and the average value of the absolute electrical impedance variation speed in a part of the chest with said slopes being relevant to two different patients examined at different physical activity levels.
Figure 9:
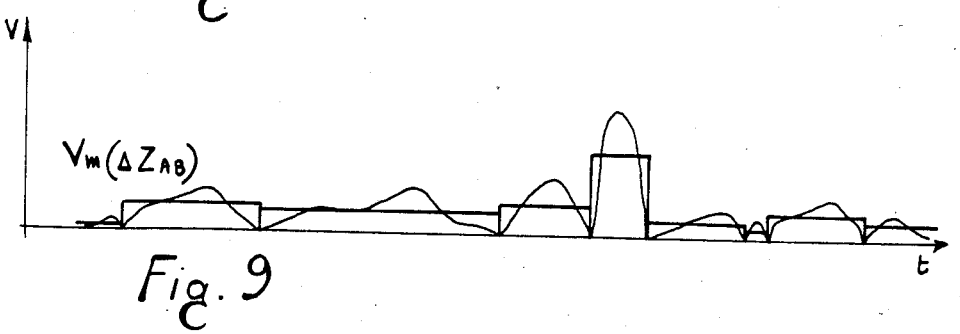

Block 3 is made up by a low-pass filter with a time constant of a few tens of seconds, e.g. approx. 30 seconds. The task of this block is to determine the mean value or the average of the absolute values of the impedance variations with a time constant such as to minimize the ripple in the output signal and to be sufficiently fast to physiologically adjust the heart stimulation rate. Signal Vm ($\Delta Z_{AB}$) corresponding to the mean value of the variation of the input signal, as shown in FIG. 9, is available at block 3 output. Data has been collected which shows that signal Vm ($\Delta Z_{AB}$) is proportionally dependent on the minute ventilation (FIG. 4) which is the physiologic variable driving the pacemaker stimulation/inhibition rate according to the present invention. We referred to the absolute values of the variations of the impedance but, likewise, reference could be made either only to the positive increases or only to the negative increases, having to avoid calculating the whole signal with the relevant polarities as the mean value would always be zero, in fact during the respiration it is agreed that the gas volume inhaled on average is well balanced with that exhaled. FIG. 4 shows the two slopes R1 and R2 which outline the correlation between minute ventilation VE (1/min) and the output signal Vm ($\Delta Z_{AB}$) from block 3 with the two slopes being relevant to two different patients examined at different activity levels. According to what has been expounded and what is shown in FIG. 4, it can be stated that output signal Vm ($\Delta Z_{AB}$) from block 3 is proportional to minute ventilation with a different proportional coefficient characterizing each patient. This coefficient can be easily ascertained if the minute ventilation of the patient during physical activity is evaluated by traditional means together with block 3 output.

Block 4 is a programmable correlator that via a telemetry link associates two values Vm1 ($\Delta Z_{AB}$) and Vm2 ($\Delta Z_{AB}$) of the output signal from block 3, which are "a priori" programmable or obtained in two different physical activity situations of the patient, with two stimulation/inhibition rates (f1 and f2) of the pacemaker circuit. The rates define a possible operational mode of the pacemaker on the basis of which f1 and f2 may, not necessarily but possibly, coincide with the minimum and maximum working rates of the pacer. The stimulation/inhibition rate (f) indication sent to block 5 is proportional to the signals Vm ($\Delta Z_{AB}$) dynamically performed by block 4.

Block 5 represents a typical pacemaker circuit well known to persons skilled in the art, realized in such a way as to guarantee the stimulation/inhibition rate (f) sent by the previous block 4. With reference to FIGS. 11 and 12, there is described now, as non-limiting example, a possible circuitry realization of block 2. The signal V ($Z_{AB}$) coming from block 1 is made up by pulses the amplitude of which is proportional to the impedance cyclically detected between electrodes A and B. SH1 and SH2 indicate two sample and holds whereas AMP-1 indicates a differential amplifier. If SH1 stores the amplitude of the $n^{th}$ of D pulses, SH2 stores the amplitude of $N^{th}-1$ pulse. A CK time signal synchronous with the pulses of block 1 first sends the output signal from SH1 to SH2 and then, after a delay due to DEL component, is stores in SH1 the new value of $n^{th}+1$ pulse amplitude. At this point AMP-1 performs the difference between $n^{th}$ amplitude stored in SH2, after the transfer performed by CK, and $n^{th}+1$ amplitude stored in SH1 and so on with the following pulses. D1 signal coming out of AMP-1 is shown in FIG. 12.

It is understood that blocks 3 and 4 are not described in every constructional detail as they can be easily realized by any expert in the field, taking into consideration the role they are designed to play. Blocks 2-3 and 4 can be realized with analog and/or digital or microprocessor based circuits.

Although this invention is disclosed within the context of a single chamber demand pacemaker, the same invention can be applied to other pacing modalities, including the so called double chamber ones (DVI) or (DDD), which maintain the atrioventricular sequentiality, or even applied to other therapeutic or diagnostic, portable or implantable devices or to artificial organs, for example to an artificial heart, operating in response to the minute ventilation of the patient. It is therefore to be underlined that the invention is not confined to the given examples, but it can be considerably changed or modified without altering the guiding principle above expounded and described and hereafter claimed.

We claim:

1. An implantable rate responsive pacer arranged to be implanted in a patient and comprising: pacer control means for producing control pulses for controlling cardiac activity at a rate which is variable between selected upper and lower limits as a function of the metabolic demand of the patient; means connected to said pacer control means for producing heart stimulation pulses in response to the control pulses; and measurement circuit means responsive to respiratory activity of the patient for producing a signal representative of the change in volume of air in the patient's lungs, corresponding to pulmonary minute ventilation, that is the quantity of air inhaled by the patient in unit time, said measurement circuit means being connected to said pacer control means for controlling the rate of the control pulses on the basis of the signal.

2. The pacer of claim 1 wherein said measurement circuit means comprise means for detecting variations with respect to time in the geometry of at least part of the chest of the patient due to pulmonary activity.

3. The pacer of claim 2 wherein said means for detecting variations comprise two electrodes implantable for monitoring such variations in chest geometry, and monitoring means connected to said electrodes for monitoring the electrical impedance present between said electrodes, and wherein said measurement circuit means further comprise signal processing means connected to said monitoring means for producing the signal dependent on minute ventilation, and wherein said electrodes are arranged to be placed in a position which guarantees that the activity monitored is substantially unaffected by movements other than respiration.

4. The pacer of claim 3 further comprising an implantable conductive case constituting the other one of said electrodes, and wherein said one of said electrodes is arranged to be implanted at a selected distance from said case.

5. The pacer of claim 3 further comprising an implantable conductive case having: two electrically conductive parts each constituting a respective one of said electrodes; and means electrically insulating said two conductive parts from one another.

6. The pacer of claim 3 wherein said monitoring means comprise means for monitoring the impedance at regularly spaced sampling times.

7. The pacer of claim 6 wherein the sampling times occur at a rate of approximately 10 Hz.

8. The pacer of claim 6 wherein: said monitoring means comprise an impedance/voltage converter for producing signal pulses $V(Z_{AB})$ which correspond in amplitude to the impedance present between said electrodes at successive sampling times; and said signal processing means comprise a calculating circuit producing a first signal $V'(\Delta A_{AB})$ representing the absolute values of the amplitude variations between successive signal pulses, and low-pass filter means having a time constant of a few tens of seconds and connected to said calculating circuit for producing a second signal $Vm(\Delta Z_{AB})$ which is based on the first signal and which represents the mean values or the average of the absolute values of the amplitude variations between successive signal pulses, said second signal constituting said signal dependent on pulmonary minute ventilation.

9. The pacer of claim 8 further comprising a programmable correlation connected to receive the second signal from said filter means and for associating two selected values of said second signal with two respective control pulse rate values, whereby the rate at which cardiac activity is controlled depends on the value of said second signal.

10. A control circuit for an active device implantable in a patient, the active device being operable at a controllable rate, and said control circuit producing an output signal which controls the operating rate of the active device, said control circuit comprising: means for detecting variations with respect to time in the geometry of at least part of the chest of the patient due to pulmonary ventilation and for producing a first signal representative of such variations; and circuit means connected to said means for detecting variations, and responsive to the first signal, for producing a second signal which is representative of the change in volume of air in the patient's lungs, corresponding to the patient's minute ventilation and which constitutes the output signal from said control circuit.

11. The control circuit of claim 10 wherein said means for detecting variations comprise two electrodes implantable for monitoring such variations in chest geometry, and monitoring means connected to said electrodes for monitoring the electrical impedance present between said electrodes, and wherein said circuit means comprise signal processing means connected to said monitoring means for producing the signal dependent on minute ventilation, and wherein said electrodes are arranged to be placed in a position which guarantees that the activity monitored is substantially unaffected by movements other than respiration.

12. The control circuit of claim 11 further comprising an implantable conductive case constituting the other one of said electrodes, and wherein said one of said electrodes is arranged to be implanted at a selected distance from said case.

13. The control circuit of claim 11 further comprising an implantable conductive case having: two electrically conductive parts each constituting a respective one of said electrodes; and means electrically insulating said two conductive parts from one another.

14. The control circuit of claim 11 wherein said monitoring means comprise means for monitoring the impedance at regularly spaced sampling times.

15. The control circuit of claim 14 wherein the sampling times occur at a rate of approximately 10 Hz.

16. The control circuit of claim 14 wherein: said monitoring means comprise an impedance/voltage converter for producing signal pulses $V(Z_{AB})$ which corresponds in amplitude to the impedance present between said electrodes at successive sampling times; and said signal processing means comprise a calculating circuit producing a first signal $V'(\Delta Z_{AB})$ representing the absolute values of the amplitude variations between successive signal pulses, and low-pass filter means having a time constant of a few tens of seconds and connected to said calculating circuit for producing a second signal $Vm(\Delta Z_{AB})$ which is based on the first signal and which represents the mean value or the average of the absolute values of the amplitude variations between successive signal pulses, said second signal constituting said signal dependent on pulmonary minute ventilation.

17. The control circuit of claim 16 further comprising a programmable correlation connected to receive the second signal from said filter means and for associating two selected values of said second signal with two respective control pulse rate values, whereby the rate at which the active device operates is controlled in dependence on the value of said second signal.

* * * * *